United States Patent [19]

Rotzoll et al.

[11] 4,233,234

[45] Nov. 11, 1980

[54] CONTINUOUS MANUFACTURE OF AN AQUEOUS SOLUTION OF A SALT OF AN ALKANEDICARBOXYLIC ACID AND AN ALKANEDIAMINE

[75] Inventors: Rudi-Heinz Rotzoll, Limburgerhof; Paul Duffner; Ernst Dietl, both of Ludwigshafen; Georg Pilz, Neustadt; Gerhard Thiel, Ludwigshafen, all of Fed. Rep. of Germany

[73] Assignee: BASF Aktiengesellschaft, Fed. Rep. of Germany

[21] Appl. No.: 914,925

[22] Filed: Jun. 12, 1978

[30] Foreign Application Priority Data

Jun. 27, 1977 [DE] Fed. Rep. of Germany ....... 2728818

[51] Int. Cl.$^3$ ............................................. C07C 87/14
[52] U.S. Cl. ................................. 260/501.2; 528/335
[58] Field of Search ....................................... 260/501.2

[56] References Cited

U.S. PATENT DOCUMENTS

| | | | |
|---|---|---|---|
| 2,130,947 | 9/1938 | Carothers | 260/501.2 |
| 3,294,758 | 12/1966 | Gabler | 260/501.2 X |
| 3,294,759 | 12/1966 | Gabler | 260/501.2 X |
| 3,952,051 | 4/1976 | Ogawa et al. | 260/501.2 |

FOREIGN PATENT DOCUMENTS

| | | |
|---|---|---|
| 2403178 | 8/1974 | Fed. Rep. of Germany . |
| 47-25119 | 10/1972 | Japan ..................................... 260/501.2 |
| 1034307 | 6/1966 | United Kingdom . |

*Primary Examiner*—G. T. Breitenstein
*Attorney, Agent, or Firm*—Keil & Witherspoon

[57] ABSTRACT

A process for the continuous preparation of an aqueous solution of a salt of an alkanedicarboxylic acid of 6 to 12 carbon atoms and an alkanediamine of 6 to 12 carbon atoms by reacting the particular alkanedicarboxylic acid with the particular alkanediamine in an aqueous solution of the salt to be prepared. The aqueous salt solution is recycled from a first mixing zone via a transport zone and a second mixing zone into the first mixing zone, liquid alkanediamine and an aqueous solution of alkanedicarboxylic acid are introduced between the first and second mixing zones. Less than the equivalent amount of alkanediamine is introduced, the remaining amount of liquid alkanediamine is added after the second mixing zone, and aqueous salt solution is taken off the first mixing zone at the rate at which it is formed. The salt prepared is used for the manufacture of a nylon.

8 Claims, 1 Drawing Figure

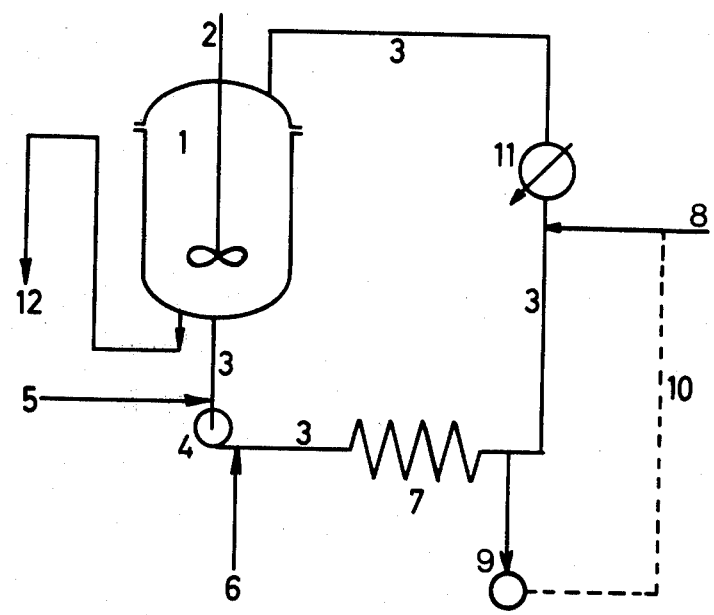

CONTINUOUS MANUFACTURE OF AN AQUEOUS SOLUTION OF A SALT OF AN ALKANEDICARBOXYLIC ACID AND AN ALKANEDIAMINE

The present invention relates to a process for the continuous manufacture of an aqueous solution of a salt of an alkanedicarboxylic acid of 6 to 12 carbon atoms and an alkanediamine of 6 to 12 carbon atoms by reacting the alkanedicarboxylic acid with the alkanediamine in an aqueous solution of the salt to be prepared.

As disclosed in the laid-open documents of Netherlands Patent Application No. 65/07,519, a salt of a dicarboxylic acid and a diamine, e.g. hexamethylenediammonium adipate, is produced by reacting the dicarboxylic acid with the diamine in an alcoholic medium, e.g. methanol. The resulting salt precipitates from the solution and is isolated by centrifuging. Since methods employing volatile inflammable solvents are undesirable in industrial practice, methods whereby such salts are produced from aqueous solutions have also already been used. According to German Laid-Open Application DOS No. 2,403,178, a salt of a dicarboxylic acid and a diamine is obtained by starting from an aqueous solution of the salt to be prepared, which solution contains excess dissolved dicarboxylic acid, and then neutralizing the solution with the diamine. The salt then precipitates from the aqueous solution, and fluctuations in the pH of the aqueous solution have no adverse effect on the quality of the salt which precipitates. However, in preparing an aqueous solution of such a salt, the dicarboxylic acid and diamine must be used in strictly equivalent amounts so as to avoid an excess of either component, since such excess interferes with the polycondensation. Furthermore, solid salts are very troublesome to handle. Hence, it has become industrial practice to use an aqueous solution of a salt of the dicarboxylic acid and the diamine for the polycondensation.

It is an object of the present invention to prepare an aqueous solution of a salt of a dicarboxylic acid and a diamine by a continuous method under conditions which maintain an equivalent ratio.

We have found that this object is achieved by a continuous process for the manufacture of an aqueous solution of a salt of an alkanedicarboxylic acid of 6 to 12 carbon atoms and an alkanediamine of 6 to 12 carbon atoms, comprising the reaction of equivalent amounts of the alkanedicarboxylic acid with the alkanediamine in an aqueous solution of the salt to be prepared, wherein the aqueous salt solution is recycled from a first mixing zone via a transport zone and a second mixing zone into the first mixing zone, liquid alkanediamine and an aqueous solution of alkanedicarboxylic acid are introduced between the first and second mixing zones, with the proviso that less than the equivalent amount of alkanediamine is introduced, the remaining amount of liquid alkanediamine is added after the second mixing zone, and aqueous salt solution is taken from the first mixing zone as product at the rate at which it is formed.

The novel process has the advantage that it does not produce any mother liquors which then require treatment. Furthermore, the process is very flexible and easily controlled. It is therefore exceptionally suitable for industrial operation. The novel process permits the continuous manufacture of large amounts, with little expenditure on apparatus.

One of the starting materials used is an alkanedicarboxylic acid of 6 to 12 carbon atoms, a straight-chain $\alpha,\omega$-alkanedicarboxylic acid having the said number of carbon atoms being preferred. Examples of suitable dicarboxylic acids are adipic acid, azelaic acid, suberic acid, sebacic acid, decanedicarboxylic acid and dodecanedicarboxylic acid. Adipic acid and sebacic acid have become industrially particularly important.

The other starting material used in an alkanediamine of 6 to 12 carbon atoms, a straight-chain $\alpha,\omega$-alkanediamine having the said number of carbon atoms being preferred. Examples of suitable alkanediamines are hexamethylenediamine, octamethylenediamine, decamethylenediamine and dodecanemethylenediamine. Hexamethylenediamine has become industrially particularly important.

Accordingly, the preferred salts are hexamethylenediammonium adipate and hexamethylenediammonium sebacate. The concentration of the aqueous solution of the salts prepared by the process is as a rule from 45 to 65% by weight, especially from 55 to 65% by weight.

The particular alkanedicarboxylic acid to be used is reacted with the appropriate alkanediamine in an aqueous solution of the particular salt to be prepared. Of course the concentration of the aqueous salt solution used corresponds to that of the product.

The aqueous salt solution is recycled from a first mixing zone via a transport zone and a second mixing zone into the first mixing zone. Advantageously, the amount of salt solution present in the first mixing zone is from 2 to 3 times the amount present in all the remaining zones and lines. As a rule, the first mixing zone is a stirred kettle or a suitable apparatus with mixing devices, e.g. circulating pumps, but it is important to ensure that the first mixing zone has a sufficient buffer capacity compared to the remaining zones. A continuously delivering pump, e.g. a gear pump, is advantageously used as the transport zone. The second mixing zone is advantageously constructed so as to ensure rapid and effective mixing of the medium flowing through it by deflectors and/or baffles. Advantageously, the amount circulated per hour is from 40 to 80 times the content of the first mixing zone.

Between the first and second mixing zones, the alkanediamine is introduced as a liquid and the alkanedicarboxylic acid as an aqueous solution. Advantageously, the alkanediamine is used as a melt. However, it is also possible to liquefy the alkanediamine by adding a small amount of water, e.g. up to 20% by weight. The alkanedicarboxylic acid is advantageously introduced as an aqueous solution of from 48 to 55% strength by weight. Of course, the total amount of water introduced must be such that after combination the resulting solution of a salt of the alkanedicarboxylic acid and the alkanediamine has the desired concentration. The amount of alkanediamine introduced is selected to be less than the required equivalent amount, based on the amount of dicarboxylic acid, advantageously from 95 to 99 mole% of the equivalent amount.

Advantageously, the alkanediamine is first introduced, in particular on the intake side of the transport zone, and the aqueous solution of the alkanedicarboxylic acid is then introduced, preferably on the delivery side of the transport zone.

The reaction mixture, which now contains a small amount of excess alkanedicarboxylic acid, is passed through a second mixing zone in order to ensure that the salt is formed. Following the second mixing zone, the remaining amount of liquid alkanediamine required to reach the equivalence point is introduced. The equivalence point of the individual salts can be easily determined from the pH. It corresponds to pH 7.65 in the case of hexamethylenediammonium adipate and pH 7.60 in the case of hexamethylenediammonium sebacate (measured in 10% strength aqueous solution at 25° C.) It is also possible to add a slight excess, for example up to 0.5 mole%, of alkanediamine and thereby to compensate for losses of alkanediamine during the condensation. Advantageously, the remaining amount of alkanediamine is added in a further mixing zone of similar construction to the second mixing zone. It has proved advantageous if the total amount of starting materials, i.e. alkanediamine, alkanedicarboxylic acid and water, which is introduced corresponds to from 0.5 to 2 times the amount of aqueous salt solution present in the entire circulation system.

The resulting aqueous solution of a salt of an alkanedicarboxylic acid and an alkanediamine is recycled into the first mixing zone. Advantageously, the aqueous solution is first passed through a cooler. Maintaining a temperature of from 90° to 102° C. during the reaction has proved advantageous.

It is particularly advantageous to control the addition of the remaining amount of alkanediamine on the basis of the pH of the recycled aqueous salt solution. For example, this may be done by continuously withdrawing a small amount of salt solution after addition of the above starting materials, diluting the solution to 10% strength by weight, measuring the pH and controlling the amount of alkanediamine added after the second mixing zone in accordance with the measured pH. It is advantageous to use a dilute alkanediamine solution, e.g. of up to 25% strength by weight, for correcting the pH.

The reaction is as a rule carried out under atmospheric pressure or slightly superatmospheric pressure. Advantageously, an inert gas atmosphere, e.g. a nitrogen atmosphere, is maintained in the first mixing zone. The aqueous salt solution is taken off the first mixing zone, for example by means of an overflow, at the rate at which it is formed.

The accompanying drawing illustrates an example of the process of the invention.

In a circulation system comprising a stirred kettle 1 with a stirrer 2, a circulation line 3, a feed pump 4, a mixing zone 7 and a cooler 11, liquid alkanediamine is introduced on the intake side of the pump 4 through line 5 whilst an aqueous solution of the alkanedicarboxylic acid is introduced on the delivery side of the pump through line 6. The remainder of the liquid alkanediamine is introduced through line 8. A small part of the aqueous salt solution is continuously taken off through line 9 and diluted to 10% strength, and the pH is measured. The value determined is transmitted as a signal via the measuring line 10 to the feed line 8 and used to regulate the amount introduced. The resulting salt solution is taken off the system, by means of the overflow line 12, at the rate at which the solution is formed.

Aqueous solutions of a salt of an alkanedicarboxylic acid and an alkanediamine are used for the manufacture of nylons.

The Example which follows illustrates the process of the invention.

EXAMPLE

Per hour, 3.8 m³ of 52.5% strength adipic acid solution and 1.65 tonnes of molten hexamethylenediamine are introduced into a circulation system comprising a 5 m³ stirred kettle equipped with a stirrer, a gear pump, a mixing zone formed by deflectors, a cooler and a pH regulating system. Only sufficient heat of neutralization to keep the system at 98° C. is removed. 250 m³/h of nylon salt solution are circulated by means of a gear pump. 10 kg/h of nylon salt solution are taken off and diluted to 10% salt content with water. The pH of this solution is used to control the addition of 10% strength hexamethylenediamine still required to reach the equivalence point of pH 7.65. Per hour, 5.95 m³ of 63% strength nylon salt solution leave the circulation system via a constant-level siphon.

We claim:

1. A continuous process for preparing an aqueous solution of a salt of an alkanedicarboxylic acid having 6 to 12 carbon atoms and an alkanediamine having 6 to 12 carbon atoms which comprises reacting the particular alkanedicarboxylic acid with the particular alkanediamine in an aqueous solution of the salt to be prepared by (1) recycling an aqueous solution of said salt from a first mixing zone through a transport zone and then a second mixing zone back to said first mixing zone, the amount of salt solution circulated per hour being from 40 to 80 times the amount contained in said first mixing zone, (2) introducing an aqueous solution of said alkanedicarboxylic acid and less than the equivalent amount of said alkanediamine in liquid form into said recycling salt solution at a location between said first and second mixing zones, (3) introducing an additional amount of said alkanediamine in liquid form into said recycling salt solution at a location after said second mixing zone, the amount of alkanedicarboxylic acid and the total amount of alkanediamine introduced being approximately equivalent, (4) maintaining the aqueous solution at a temperature in the range of 90° C. to 102° C., and (5) removing aqueous salt solution from the first mixing zone at a rate corresponding to the rate at which it is formed.

2. A process as set forth in claim 1, wherein liquid alkanediamine is introduced on the intake side of the transport zone.

3. A process as set forth in claim 1, wherein the aqueous solution of alkanedicarboxylic acid is introduced on the delivery side of the transport zone.

4. A process as set forth in claim 1, wherein the addition of the remaining amount of liquid alkanediamine is controlled by the pH of the aqueous salt solution before re-entry into the first mixing zone.

5. A process as set forth in claim 1, wherein the amount of salt solution present in the first mixing zone is from 2 to 3 times the amount present in all the remaining zones and lines.

6. A process as set forth in claim 1, wherein the amount of alkanediamine introduced between the first and second mixing zones is from 95 to 99 mole% of the equivalent amount, based on the amount of dicarboxylic acid.

7. A process as set forth in claim 1, wherein the total amounts of alkanediamine, alkanedicarboxylic acid and water introduced in the mixing zones is from 0.5 to 2 times the amount of aqueous salt solution present in the entire circulation system.

8. A process as set forth in claim 4, wherein the pH of the aqueous salt solution is determined by withdrawing a small amount of the aqueous salt solution, diluting the solution, measuring the pH and then the remaining alkanediamine is added in an amount sufficient to reach the equivalence point as determined by said pH.

* * * * *